United States Patent
Mehta

(10) Patent No.: US 9,884,148 B2
(45) Date of Patent: Feb. 6, 2018

(54) ANGULAR CAP FOR DISPENSING LIQUIDS

(71) Applicant: Ketan C Mehta, Santa Rosa, CA (US)

(72) Inventor: Ketan C Mehta, Santa Rosa, CA (US)

(73) Assignee: NeilMed Pharmaceuticals, Inc., Santa Rosa, CA (US)

( * ) Notice: Subject to any disclaimer, the term of this patent is extended or adjusted under 35 U.S.C. 154(b) by 79 days.

(21) Appl. No.: 14/862,067

(22) Filed: Sep. 22, 2015

(65) Prior Publication Data

US 2016/0114096 A1 Apr. 28, 2016

Related U.S. Application Data

(60) Provisional application No. 62/053,515, filed on Sep. 22, 2014, provisional application No. 62/053,531, filed on Sep. 22, 2014.

(51) Int. Cl.
*A61M 31/00* (2006.01)
*A61M 3/02* (2006.01)
*A61H 35/04* (2006.01)

(52) U.S. Cl.
CPC .......... *A61M 3/0279* (2013.01); *A61H 35/04* (2013.01); *A61M 3/0241* (2013.01); *A61M 3/0262* (2013.01); *A61M 2210/0618* (2013.01); *A61M 2210/0662* (2013.01)

(58) Field of Classification Search
CPC ............................. A61M 3/0241; A61H 35/04
See application file for complete search history.

(56) References Cited

U.S. PATENT DOCUMENTS

| | | | |
|---|---|---|---|
| 2,135,052 A | 11/1938 | Rose | |
| 2,330,019 A * | 9/1943 | Vaughn | A61J 9/00 215/11.1 |
| 2,608,841 A | 9/1952 | Rice | |
| 5,788,683 A | 8/1998 | Martin | |
| 6,156,017 A | 12/2000 | Shieh | |

(Continued)

FOREIGN PATENT DOCUMENTS

WO WO 2013/124491 8/2013
WO WO 2013/164759 11/2013

OTHER PUBLICATIONS

Authorized officer Lee W. Young, International Search Report and Written Opinion in PCT/US2015/051550, dated Jan. 6, 2016, 11 pages.

(Continued)

*Primary Examiner* — Nathan R Price
*Assistant Examiner* — John Doubrava
(74) *Attorney, Agent, or Firm* — Kelley Drye & Warren LLP

(57) ABSTRACT

A cap and container assembly is disclosed which may be used for human body cavity irrigation or other liquid dispensing activities. The cap may include a first channel extending from a base through a neck portion to an opening in a tip portion of the cap. A side body defining a second channel may extend from the first channel near the neck portion of the cap to an opening at a distal end of the side body. An axial dimension of the tip portion may extend at an angle relative to an axial dimension of the neck portion. Liquid may flow out of the first channel under the influence of gravity and as a result of control of air flow into the second channel.

22 Claims, 11 Drawing Sheets

(56) References Cited

U.S. PATENT DOCUMENTS

| | | | | |
|---|---|---|---|---|
| 6,241,705 B1* | 6/2001 | Ko-Wen | ............... | A61M 3/0241 |
| | | | | 604/73 |
| 6,540,718 B1* | 4/2003 | Wennek | ................. | A61H 35/04 |
| | | | | 604/275 |
| 2006/0118580 A1* | 6/2006 | Spencer | ............ | B05C 17/00516 |
| | | | | 222/327 |
| 2009/0247941 A1* | 10/2009 | Lu | ....................... | A61M 3/0262 |
| | | | | 604/73 |
| 2010/0282246 A1 | 11/2010 | Djupesland et al. | | |

OTHER PUBLICATIONS

European Search Report in European Application No. 15843448.0, dated Aug. 23, 2017, 8 pages.

\* cited by examiner

ANGULAR CAP FOR DISPENSING LIQUIDS

CROSS-REFERENCE TO RELATED APPLICATIONS

This application relates to, and claims the benefit of the earlier filing date and priority of U.S. Provisional Patent Application No. 62/053,515, filed on Sep. 22, 2014, entitled "Angular Cap for Dispensing Liquids," and U.S. Provisional Patent Application No. 62/053,531, filed on Sep. 22, 2014, entitled "Collapsible Bottle Apparatus and System."

FIELD OF THE INVENTION

The present invention relates generally methods and devices for dispensing liquids, including but not limited to lavage methods and devices.

BACKGROUND OF THE INVENTION

Liquid dispensing container/cap assemblies for dispensing liquids are known. For example, nasal rinsing and/or other body cavity irrigation assemblies and methods are disclosed in U.S. Pat. Nos. 6,669,059 and 6,520,384. In these assemblies the cap may have a cylindrical lower portion, a rounded convex upper portion curving away from an axially aligned opening located in the uppermost surface of the upper portion, an open lower end, and a tubular conduit connected to the uppermost interior surface of the upper portion and having a hollow center axially aligned with the opening located in the upper portion. The container of these assemblies may have flexible sidewalls and an axially aligned neck configured to connect to the cap with a liquid tight connection. The conduit of the cap can extend into the container when the cap and container are joined together, or a flexible tube can be connected to the conduit, which flexible tube extends into the container.

The assemblies disclosed in the '059 and '384 patents may be used in the following manner. The user bends forward to a comfortable level, tilting the head slightly down and applies the cap snugly against the left nostril with the cap upper opening directed into the left nasal passage. The container may be squeezed to force liquid to enter the left nasal passage. The process is repeated applying the cap snugly against the right nostril. The liquid that was injected into the nasal passages will drain from the nasal passages or the mouth. The user then gently blows the nose. Any unused portion of the liquid may be discarded and the dispenser assembly should be cleaned. Thus, the assemblies disclosed in the '059 and '384 patents require the user or an assistant to squeeze the container to force liquid up into the nasal cavity as opposed to using gravity to drain the liquid out of the container.

The assemblies disclosed in the '059 and '384 patents are not effective for gravity feed of liquid to a user's nasal or other body cavity for at least two primary reasons. First, the conduit through which liquid flows out of the cap in these known assemblies is co-axial with the longitudinal axis of the liquid container. As a result, the degree to which the user would comfortably tilt her head to present her sinuses in the desired orientation to receive liquid for nasal rinsing, for example, would not permit the container to be optimally oriented to dispense liquid under the force of gravity. Accordingly, there is a need for a cap which permits the user's head to be tilted to the desired degree for nasal irrigation which also results in the liquid container being positioned in a preferred, substantially vertical, orientation for liquid dispensing under the force of gravity.

Second, the assemblies disclosed in the '059 and '384 patents do not include a cap which vents air into a container in a manner that would permit effective gravity feed of liquid to a user's nasal cavity from the container. In order for liquid to flow out of a fixed volume space (i.e., a container which is not squeezed) under the force of gravity, air must flow into the space to displace the liquid. The assemblies disclosed in the '059 and '384 patents do not permit such venting since there is only one opening in the cap through which liquid must flow out, and air must flow in. Indeed, the ability to vent air into a liquid container in a controlled, or even uncontrolled, manner when dispensing liquid under the influence of gravity is advantageous for all liquid dispensing activities, not just those associated with body cavity rinsing. Accordingly, there is a need for a cap which permits liquid to flow out and air to flow in to a liquid container simultaneously to allow effective dispensing of a liquid using gravity.

For the foregoing reasons, there is a need for apparatus and methods for dispensing a liquid to a nasal cavity in particular, but not limited to such use, which is simple to use, effective, and relatively inexpensive.

SUMMARY OF THE INVENTION

Responsive to the foregoing challenges, Applicant has developed an innovative cap having an elongated body defining a first channel extending from an opening in a base portion of the elongated body through a neck portion of the elongated body to an opening in a tip portion of the elongated body, a side body defining a second channel extending from the first channel near the neck portion of the elongated body to an opening at a distal end of the side body, wherein a terminus of the tip portion is sloped inward in a manner adapted to be received in a human body opening, wherein an axial dimension of the tip portion extends at an angle relative to an axial dimension of the neck portion, and wherein the base portion includes connection features adapted to permit the cap to be attached to a hand-held container.

Applicant has further developed an innovative

It is to be understood that both the foregoing general description and the following detailed description are exemplary and explanatory only, and are not restrictive of the invention as claimed.

BRIEF DESCRIPTION OF THE DRAWINGS

In order to assist the understanding of this invention, reference will now be made to the appended drawings, in which like reference characters refer to like elements. The drawings are exemplary only, and should not be construed as limiting the invention.

DETAILED DESCRIPTION OF EMBODIMENTS OF THE INVENTION

Figure 1:
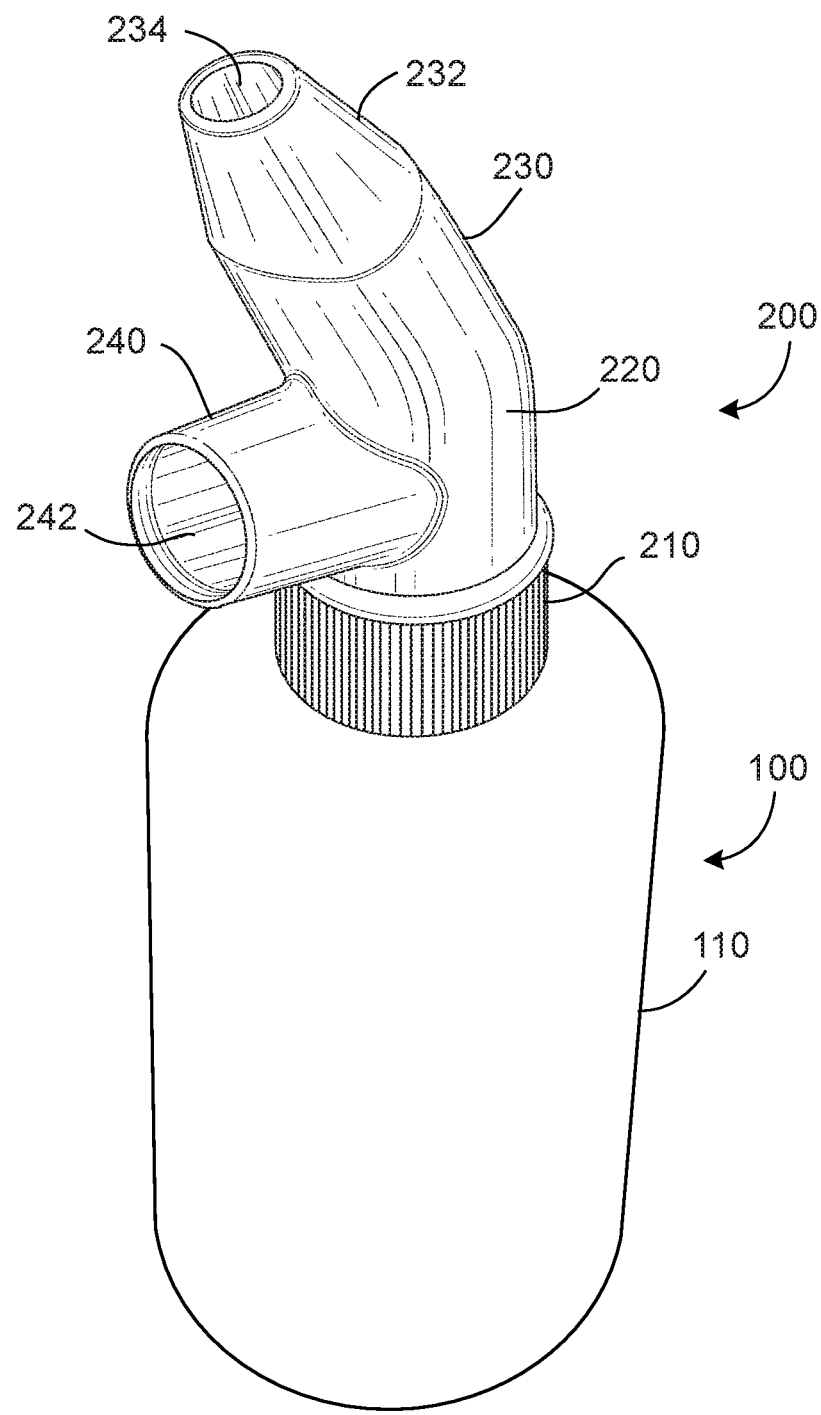
FIG. 1 is a pictorial view of a container and cap assembly in accordance with an embodiment of the present invention.

Reference will now be made in detail to apparatus and method embodiments of the present invention, examples of which are illustrated in the accompanying drawings. With reference to FIGS. 1-7, in a first embodiment of the invention, the throat wall 130 of a container 100 is connected to the base portion 210 of the elongated body of a cap 200. The throat wall 130 may be connected to the base portion 210 by any of a number of means, including but not limited to screw threads or snap-on features. The container 100 may include an outer wall 110 which defines a space 120 for containing liquid. The liquid may be dispensed from the space 120 to the cap 200 via the container throat 132. The container 100 is preferably sized to be hand-held.

The cap 200 may include an elongated body 202 defining a first channel 222 extending from an opening in the base portion 210, through a neck portion 220, and to an opening in a tip portion 230 of the elongated body. The cap 200 may further include a side body 240 defining a second channel 242 extending from the first channel 222 near the neck portion 220 of the elongated body to an opening at a distal end of the side body. The tip portion 230 may include a terminus 232 which is sloped inward so as to have a reduced dimension at its most distal end. The shape of the terminus may be adapted to be received comfortably in a human body opening, such as, for example, a nostril or ear. The foregoing reference to "near the neck portion" is intended to include the portions of the cap 200 between the base 210 and the tip portion terminus 232.

Figure 2:
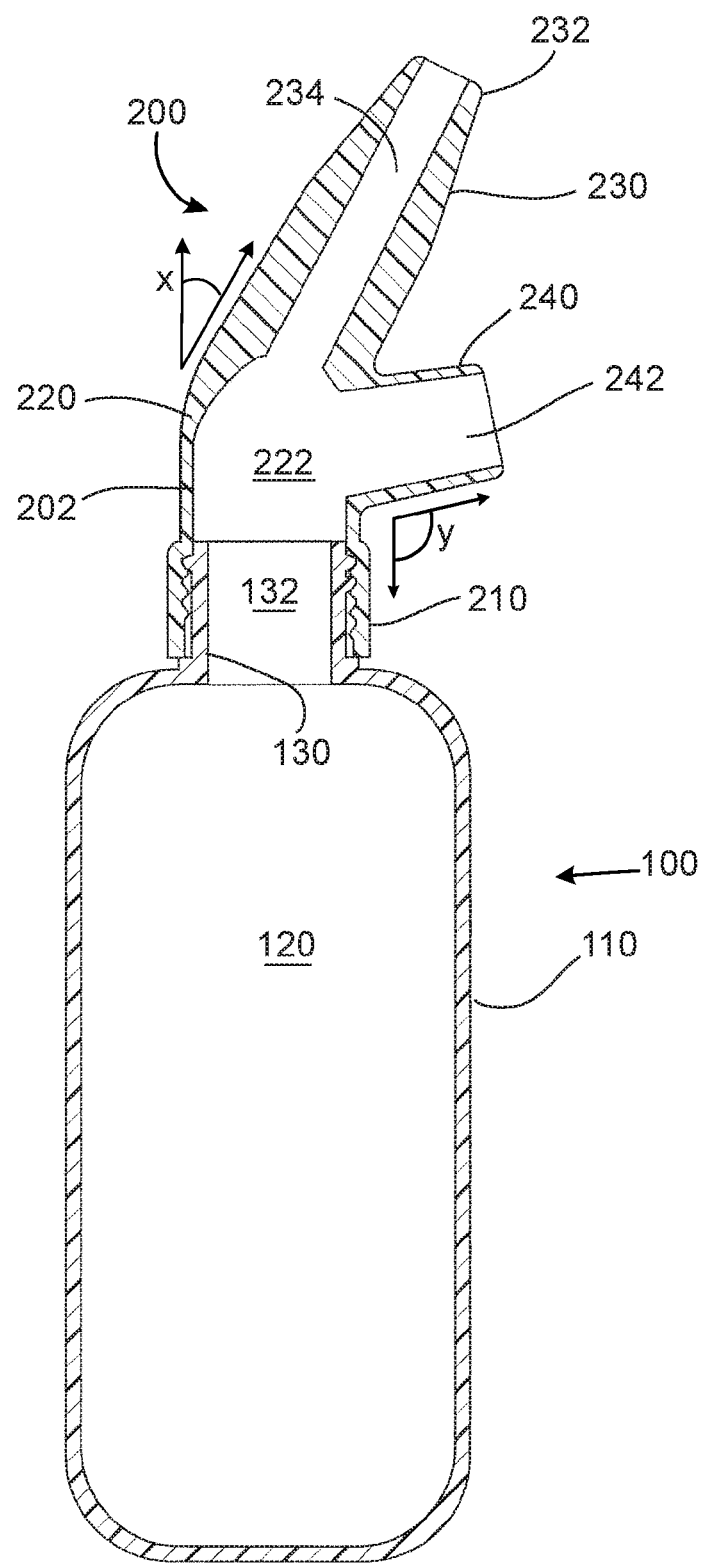
FIG. 2 is a cross-sectional view of a container and cap assembly in accordance with an embodiment of the present invention.
Figure 3A:
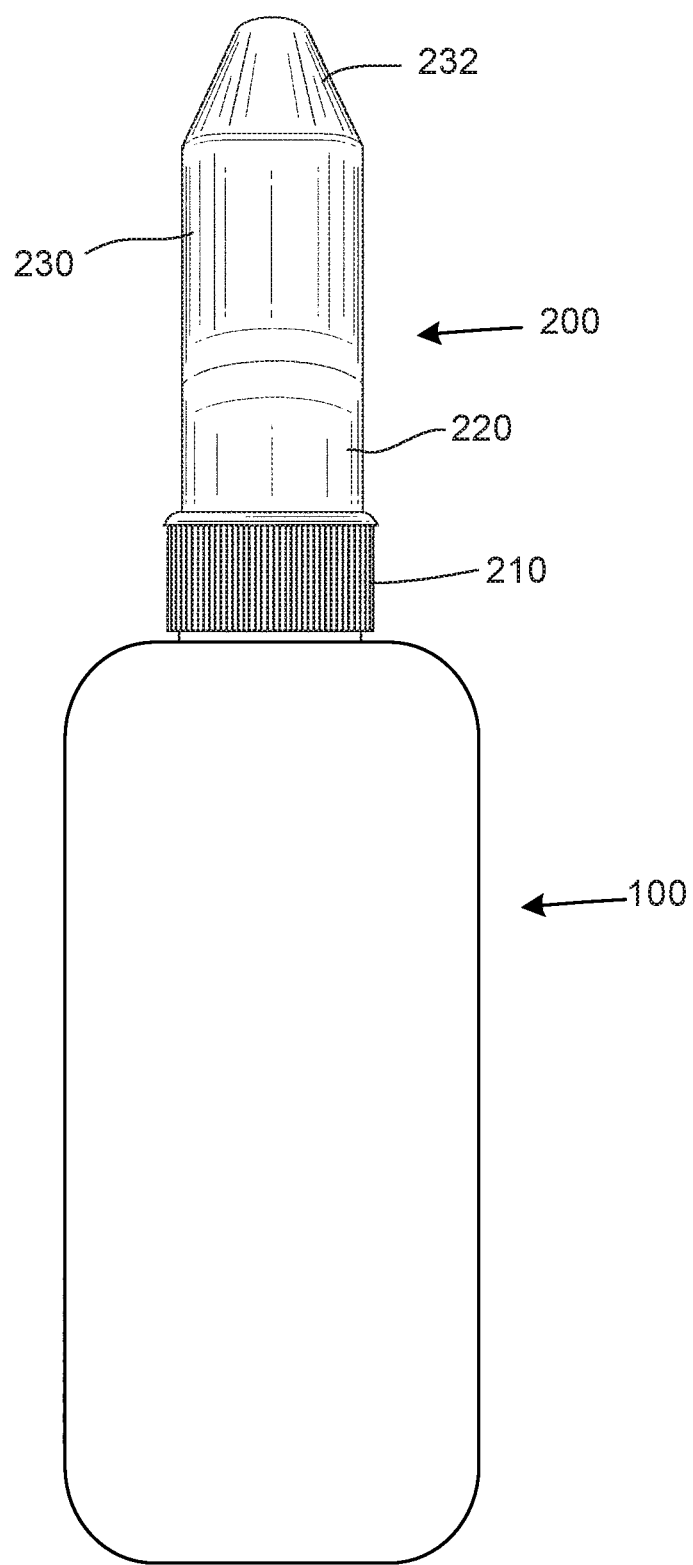
FIG. 3A is a rear elevation view of a container and cap assembly in accordance with an embodiment of the present invention.
Figure 3B:
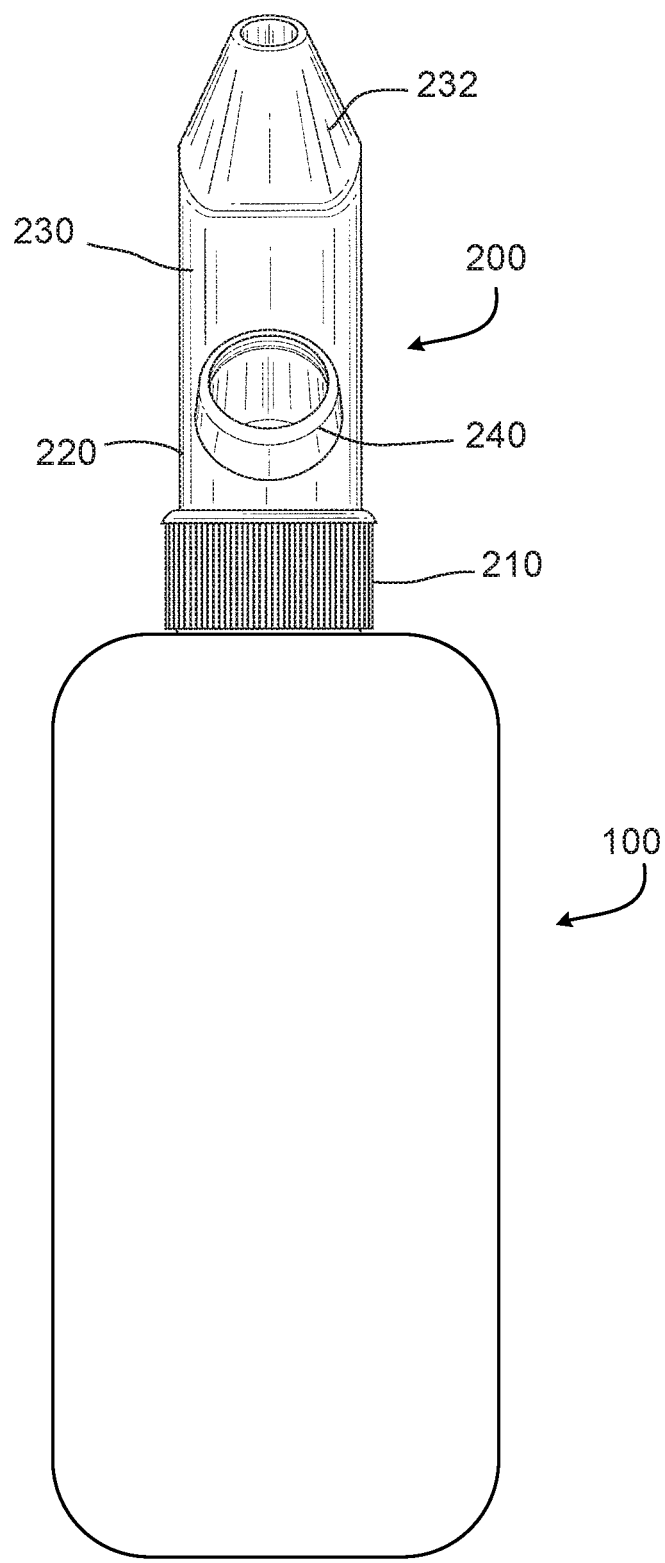
FIG. 3B is a front elevation view of a container and cap assembly in accordance with an embodiment of the present invention.
Figure 4:
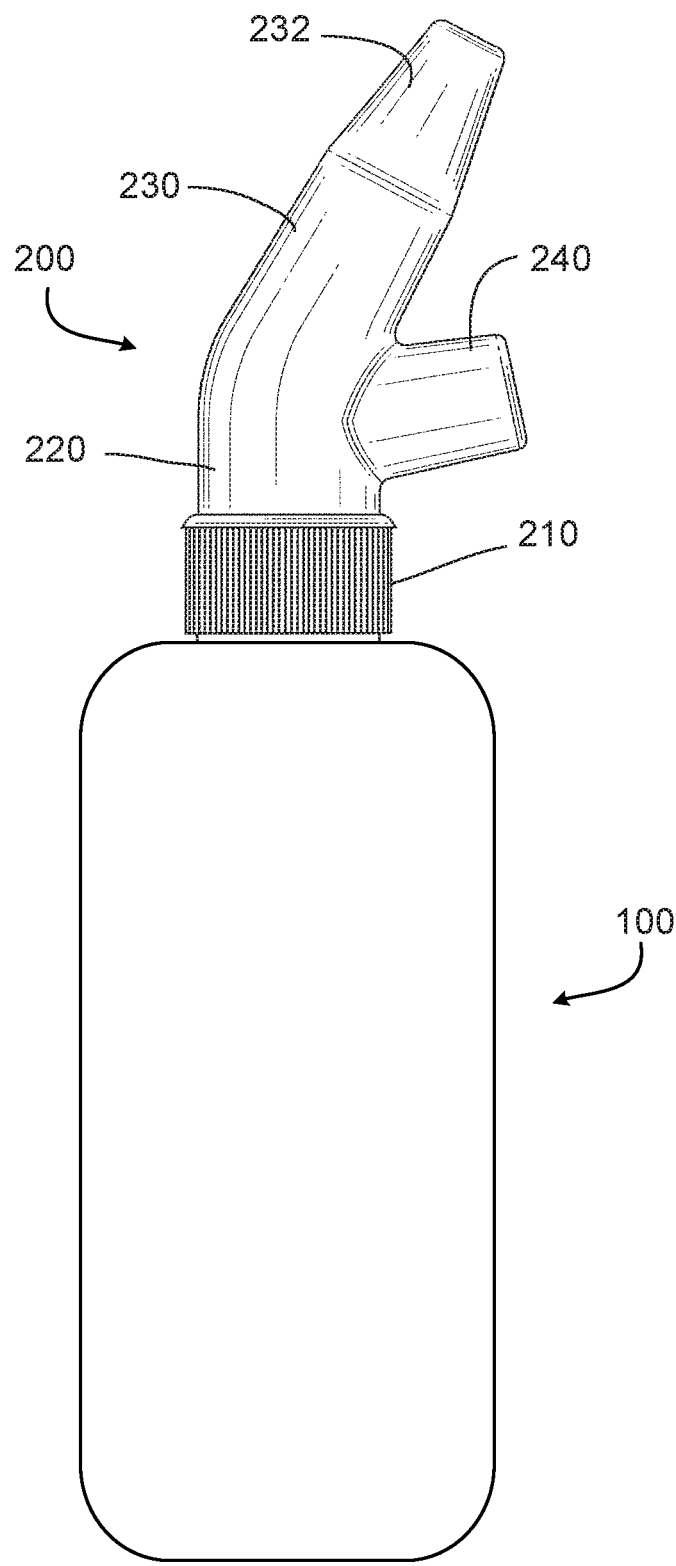
FIG. 4 is a side elevation view of a container and cap assembly in accordance with an embodiment of the present invention.
Figure 5:
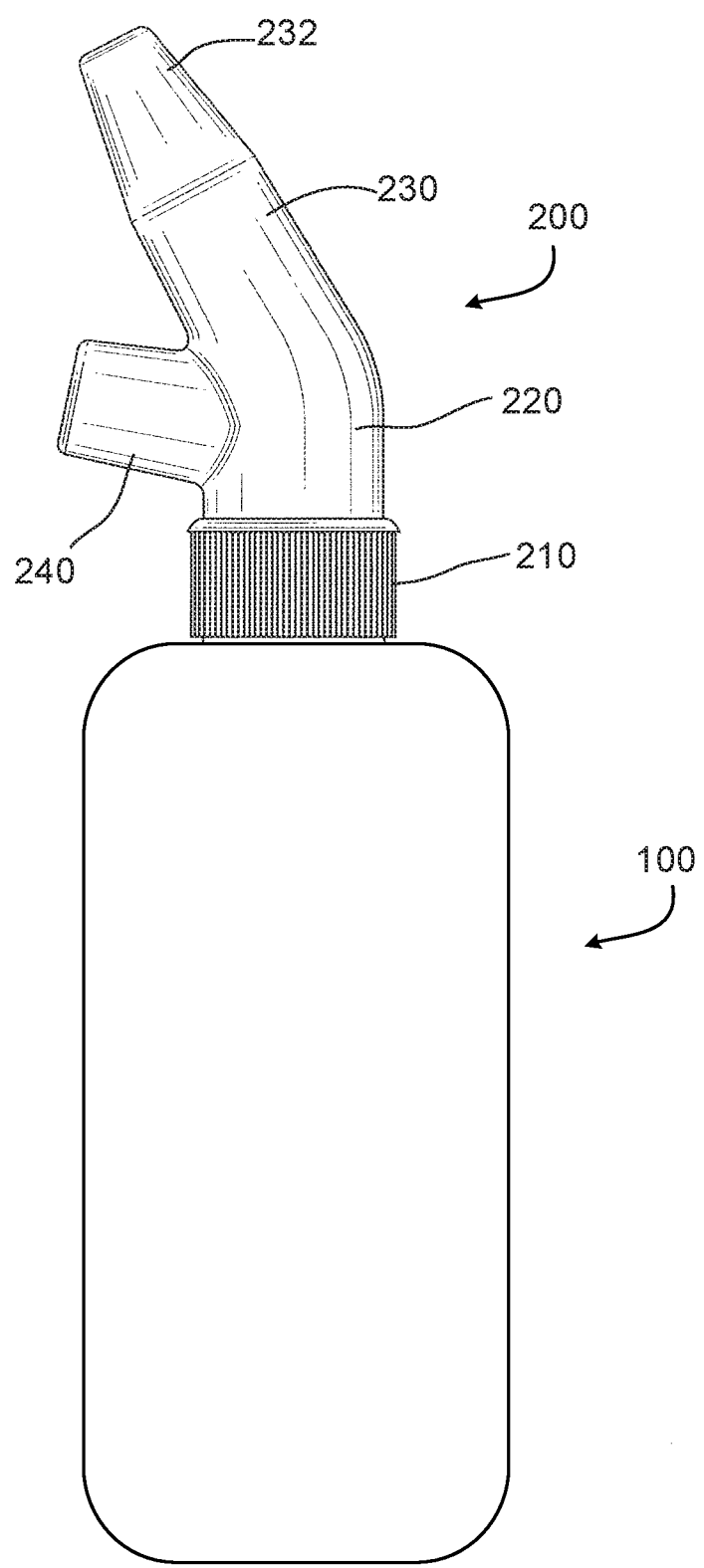
FIG. 5 is an opposing side elevation view of a container and cap assembly in accordance with an embodiment of the present invention.
Figure 6:
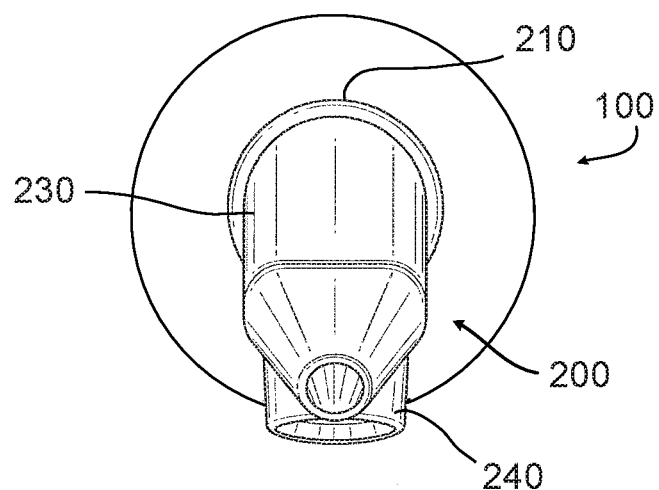
FIG. 6 is a top plan view of a container and cap assembly in accordance with an embodiment of the present invention.
Figure 7:
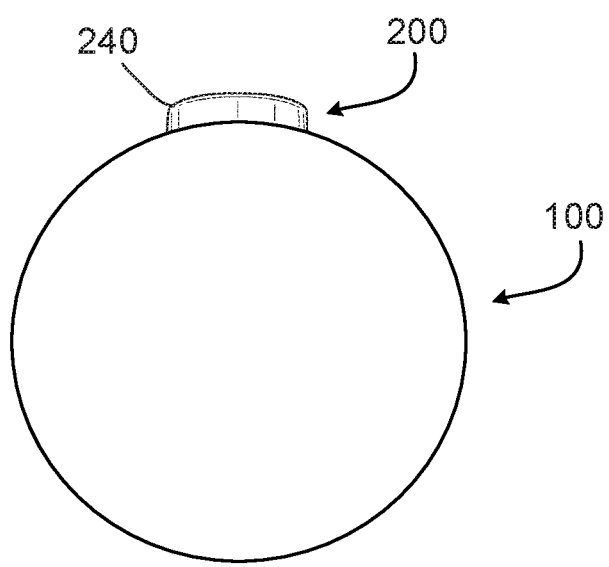
FIG. 7 is a bottom plan view of a container and cap assembly in accordance with an embodiment of the present invention.
Figure 8:
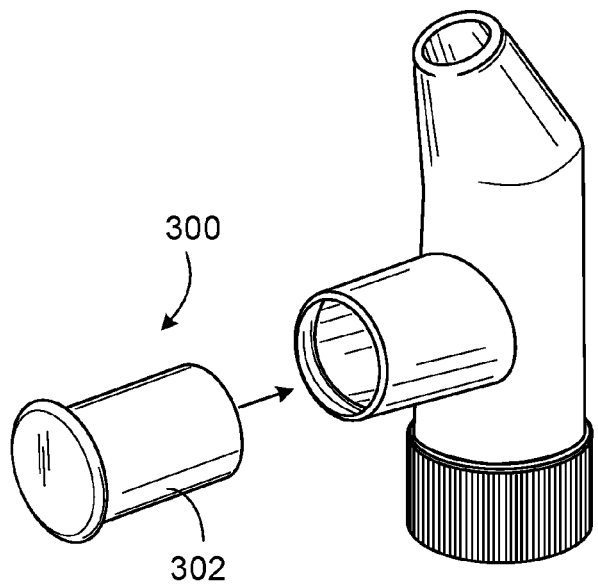
FIG. 8 is a pictorial view of a container and cap assembly including an obturator/stopper in accordance with a first alternative embodiment of the present invention.
Figure 9:
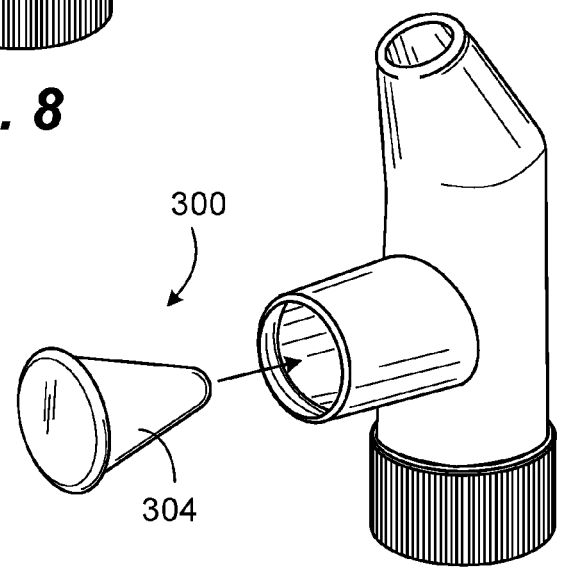
FIG. 9 is a pictorial view of a container and cap assembly including an obturator/stopper in accordance with a second alternative embodiment of the present invention.

With particular reference to FIG. 2, the tip portion 230 may have an axial dimension that extends at an angle x relative to an axial dimension of the neck portion 220, wherein angle x is in the range of between zero (0) and ninety (90) degrees. The side body 240 may have an axial dimension that extends at an obtuse angle y relative to an axial dimension of the neck portion 220. The angle x may be selected to permit the tip portion 230 to be comfortably and snuggly received in a user's body cavity, such as a nostril or ear, while at the same time permitting the container 100 to be oriented such that liquid will flow from the container under the influence of gravity. The angle y may be selected to permit a user to control the flow of air into the second channel 242 by hand when the container 100 is oriented such that liquid will flow from the container under the influence of gravity. Such control may be exercised by selectively covering the distal opening of the channel 242 with a finger, or with an obturator or stopper (explained below). It is appreciated that one or both of the tip portion 230 and the side body 240 may be flexible and capable of being adjusted to form various different angles x and y relative to the axial direction of the neck portion 220.

Figure 10:
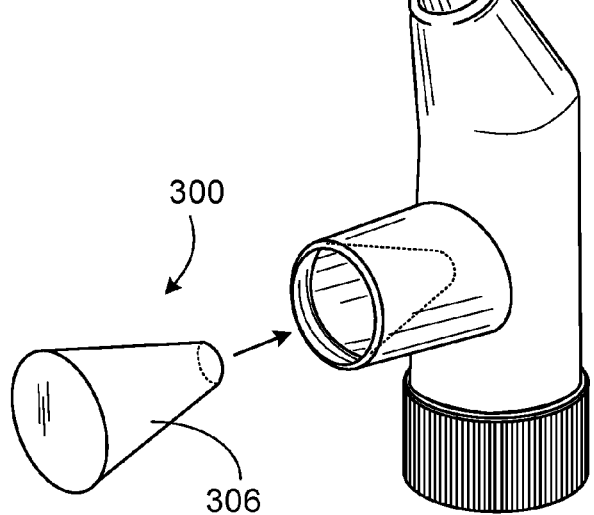
FIG. 10 is a pictorial view of a container and cap assembly including an obturator/stopper in accordance with a third alternative embodiment of the present invention.
Figure 11:
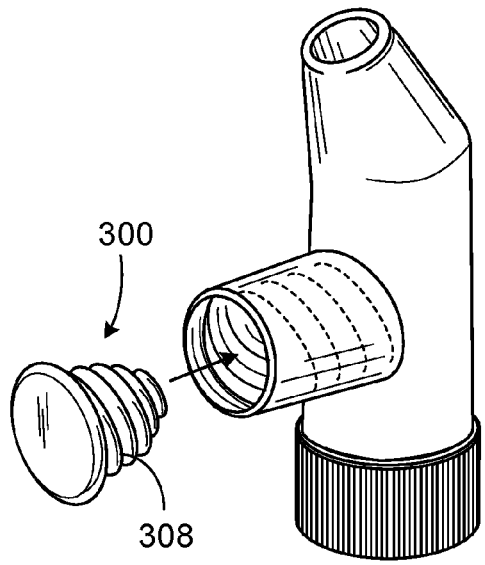
FIG. 11 is a pictorial view of a container and cap assembly including an obturator/stopper in accordance with a fourth alternative embodiment of the present invention.
Figure 12:
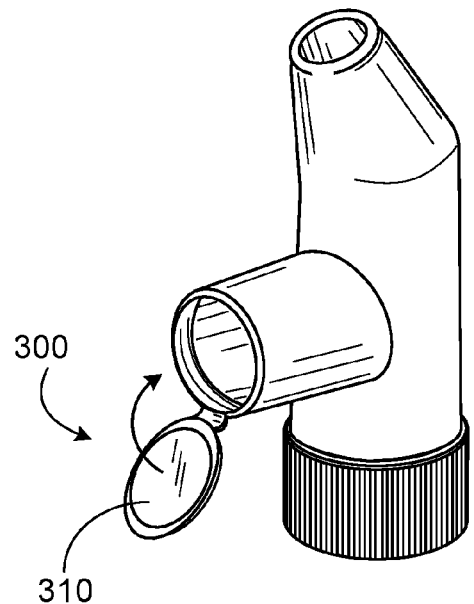
FIG. 12 is a pictorial view of a container and cap assembly including an obturator/stopper in accordance with a fifth alternative embodiment of the present invention.
Figure 13:
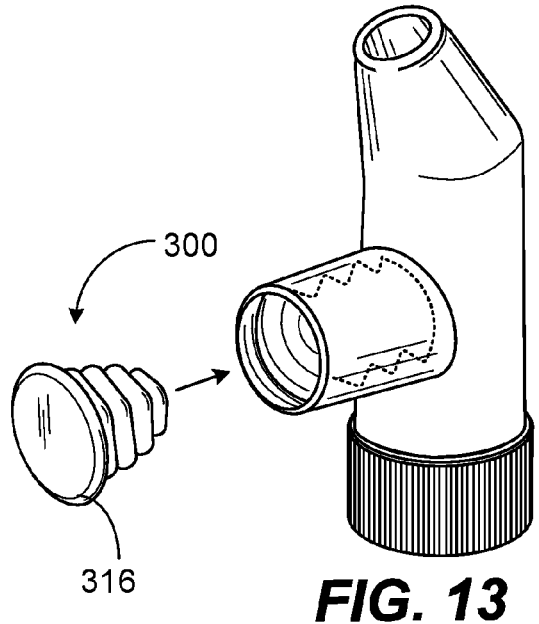
FIG. 13 is a pictorial view of a container and cap assembly including an obturator/stopper in accordance with a sixth alternative embodiment of the present invention.
Figure 14A:
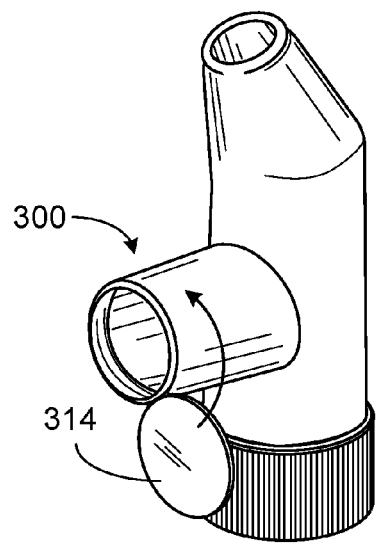
FIGS. 14A-14B are pictorial views of a container and cap assembly including an obturator/stopper in accordance with a seventh alternative embodiment of the present invention.
Figure 14B:
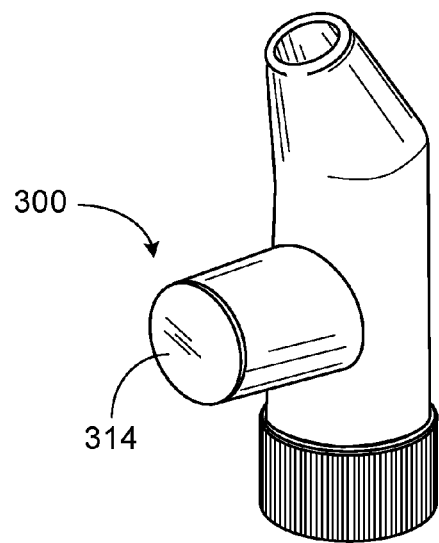

The relative diameters of the first channel 222 in the neck portion, the first channel in the tip portion 230, and the second channel 242, may be sized/adapted to permit liquid to flow from the base portion 210 of the cap 200 through the tip portion 230 under the influence of gravity while at the same time permitting air to flow into the first channel from the second channel. For example, to this end, the first channel 222 may have a reduced diameter 234 within the tip portion 230 relative to the diameter of the first channel in the neck portion 220. In a further example, the diameter of the second channel 242 may be less than the diameter of the first channel 222. In a still further example, the reduced diameter 234 within the tip portion 230 may be less than the diameter of the second channel 242. In a still further example, the diameter of the second channel 242 may vary over its length, as shown in FIG. 10.

Figure 15:
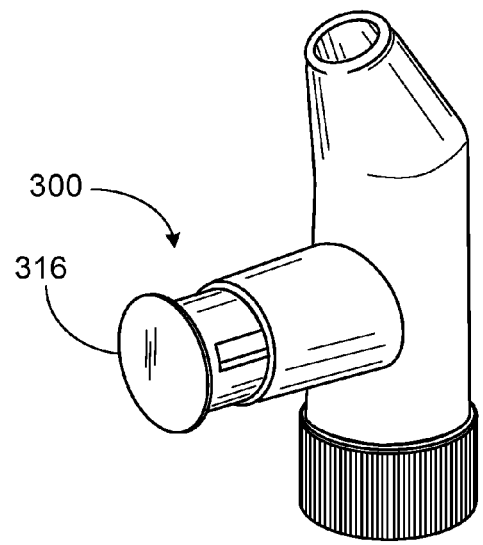
FIG. 15 is a pictorial view of a container and cap assembly including an obturator/stopper in accordance with an eighth alternative embodiment of the present invention.
Figure 16A:
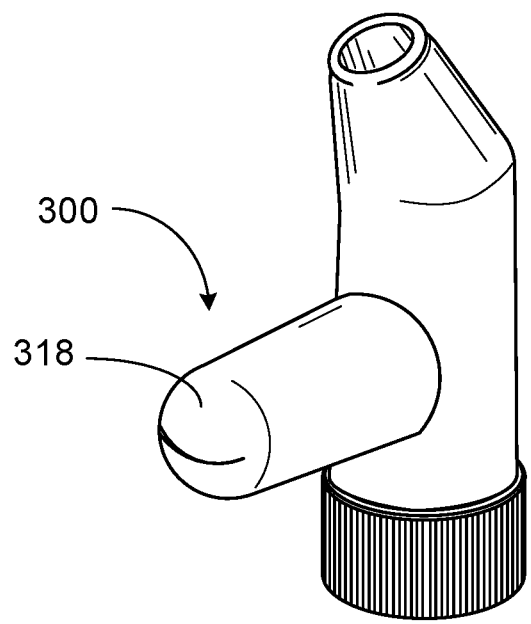
FIGS. 16A-16B are pictorial views of a container and cap assembly including an obturator/stopper in accordance with a ninth alternative embodiment of the present invention.
Figure 16B:
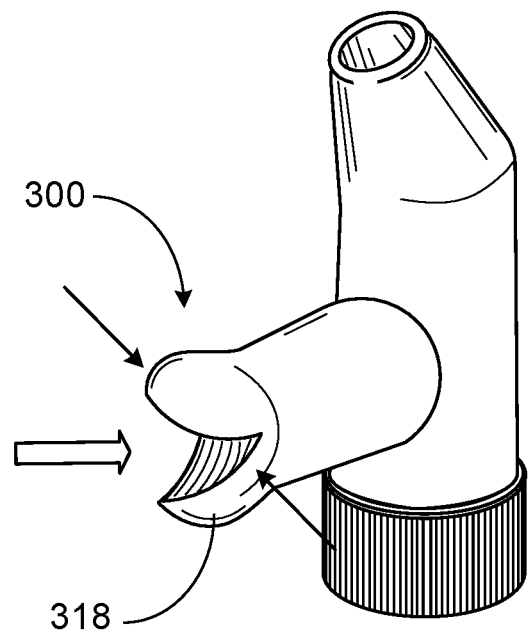

With reference to FIGS. 8-16B, the cap may also include an obturator or stopper 300 which may be provided by any of a number of different shapes, sizes and designs. Each of the illustrated obturators or stoppers may be shaped and sized to cooperate with the shape of the second channel 242 and side body 240 so as to selectively block the second channel in whole or in part. Preferably, the obturator or stopper may be adapted to be manipulated by hand to control the flow of air into the second channel 242. For example, the obturator or stopper may have a plug shape (FIG. 8, 302), a rounded cone shape (FIG. 9, 304), a frusto-conical shape (FIG. 10, 306), a threaded conical shape (FIG. 11, 308), a undulated shape (FIG. 13, 312), or a forked plug shape (FIG. 15, 316). In each of the foregoing examples, the obturator or stopper 300 may be detachable from the side body 240 of the cap 200. In further examples, the obturator or stopper 300 may be permanently connected to the side body 240 of the cap 200 by a hinge (FIG. 12, 310) and (FIGS. 14A-14B, 314), In a still further example, the obturator or stopper 300 may comprise an open and closable mouth (FIGS. 16A-16B, 318) which is permanently connected to the side body 240.

The afore-described cap 200 may improve upon or even maximize the flow of a solution or liquid out of the container 100. The following is an example of how the cap 200 may be used for a tissue irrigation application. An irrigation solution may be prepared and provided in the container 100.

The cap 200 may be connected to the container 100. The terminus 232 of the tip portion 230 may be inserted into a nasal passage, for example, on the right side (for the purposes of this example, the opening is initially inserted into the right side, but the user may begin the treatment in either side, as applicable). Next the user may tilt the head along with inserted cap to the left side such that the container 100 is inverted all while the second channel 242 of the cap 200 is blocked by a finger, obturator, or stopper. The finger, obturator, or stopper may be fully or partially removed from the second channel 242 at this point to allow solution to enter the nasal passage on the right side and come out from the left side. The user need not squeeze the container 100 since the solution should flow under the influence of gravity. The user can continue irrigation as long as needed, and the same procedure can be applied for the other nasal passage. Manipulation of the user's finger, or of the obturator or stopper may be used to regulate the flow rate of the solution out of the container 100 by regulating the flow of air into the second channel 242. If the user requires additional force of irrigation, the user can squeeze the container 100 and use a finger, obturator or plug to block solution from coming out of the second channel 242. The diameter of the second channel 242 may be selected and controlled, but not necessarily, so that the container 100 may empty under the influence of gravity in a matter of seconds. The cap 200 may be designed to facilitate the smooth flow of liquids having various viscosities, weights and temperatures. The cap 200 may be manufactured as a single component, or it may be comprised of multiple components assembled as needed.

As will be understood by those skilled in the art, the invention may be embodied in other specific forms without departing from the spirit or essential characteristics thereof. The functional elements and method steps described above are provided as illustrative examples of one technique for implementing the invention; one skilled in the art will recognize that many other implementations are possible without departing from the present invention as recited in the claims. Accordingly, the disclosure of the present invention is intended to be illustrative, but not limiting, of the scope of the invention. It is intended that the present invention cover all such modifications and variations of the invention, provided they come within the scope of the appended claims and their equivalents.

What is claimed is:

1. A cap comprising:
   an elongated body defining a first channel extending from a first opening in a base portion of the elongated body through a neck portion of the elongated body to a second opening in a tip portion of the elongated body;
   a side body defining a second channel extending from the first channel near the neck portion of the elongated body to a third opening at a distal end of the side body,
   wherein a terminus of the tip portion is sloped in a manner adapted to be received in a human body opening,
   wherein the cap defines:
      a longitudinal axis through a center of the first opening in the base portion, and
      a first plane through the first channel and the second channel,
      wherein a first portion of an exterior surface of the elongated body in the first plane forms a first acute angle with the longitudinal axis, and a second portion of the exterior surface of the elongated body, diametrically opposed to the first portion of the exterior surface of the elongated body, forms a second acute angle with an exterior surface of the side body in the first plane, and
   wherein the base portion is adapted to couple to a handheld container.

2. The cap of claim 1, wherein the first channel has a reduced diameter within the tip portion relative to a diameter in the neck portion.

3. The cap of claim 2, wherein a diameter of the second channel is less than a diameter of the first channel.

4. The cap of claim 2, wherein relative diameters of the first channel and the second channel are adapted to permit liquid to flow from the base portion to the tip portion under the influence of gravity while at the same time permitting air to flow into the first channel from the second channel.

5. The cap of claim 4, further comprising an obturator or stopper, and wherein the second channel is shaped to be selectively blocked in whole or in part by the obturator or stopper.

6. The cap of claim 5, wherein the obturator or stopper is adapted to be manipulated by hand to control the flow of air into the second channel.

7. The cap of claim 5, wherein the obturator or stopper is permanently connected to the side body.

8. The cap of claim 5, wherein the second channel is shaped to fixedly receive the obturator or stopper.

9. The cap of claim 4, wherein an axial dimension of the side body extends at an obtuse angle relative to the longitudinal axis.

10. The cap of claim 1, wherein a diameter of the second channel is less than a diameter of the first channel.

11. The cap of claim 1, wherein relative diameters of the first channel and the second channel are adapted to permit liquid to flow from the base portion to the tip portion under the influence of gravity while at the same time permitting air to flow into the first channel from the second channel.

12. The cap of claim 1, further comprising an obturator or stopper, and wherein the second channel is shaped to be selectively blocked in whole or in part by the obturator or stopper.

13. The cap of claim 12, wherein the obturator or stopper is adapted to be manipulated by hand to control the flow of air into the second channel.

14. The cap of claim 12, wherein the obturator or stopper is permanently connected to the side body.

15. The cap of claim 12, wherein the second channel is shaped to fixedly receive the obturator or stopper.

16. The cap of claim 1, wherein an axial dimension of the side body extends at an obtuse angle relative to the longitudinal axis.

17. The cap of claim 16, further comprising an obturator or stopper, and wherein the second channel is shaped to be selectively blocked in whole or in part by the obturator or stopper.

18. The cap of claim 17, wherein the obturator or stopper is adapted to be manipulated by hand to control the flow of air into the second channel.

19. The cap of claim 17, wherein the obturator or stopper is permanently connected to the side body.

20. The cap of claim 17, wherein the second channel is shaped to fixedly receive the obturator or stopper.

21. The cap of claim 1, wherein the cap defines a second plane orthogonal to the first plane, the first plane and second plane including the longitudinal axis, and the second opening and the third opening are on a common side of the second plane.

22. A cap comprising:
an elongated body defining a first channel extending from a first opening in a base portion of the elongated body through a neck portion of the elongated body to a second opening in a tip portion of the elongated body; and
a side body defining a second channel extending from the first channel near the neck portion of the elongated body to a third opening at a distal end of the side body,
wherein the cap defines:
- a longitudinal axis through a center of the first opening in the base portion,
- a first plane through the first channel and the second channel, and
- a second plane orthogonal to the first plane, the first plane and the second plane including the longitudinal axis, and
- wherein a first portion of an exterior surface of the elongated body in the first plane forms a first acute angle with the longitudinal axis, and a second portion of the exterior surface of the elongated body, diametrically opposed to the first portion of the exterior surface of the elongated body, forms a second acute angle with an exterior surface of the side body in the first plane, wherein the second opening and the third opening are on a common side of the second plane, and
wherein the base portion is adapted to couple to a hand-held container.

* * * * *